US005351686A

United States Patent [19]

Steuer et al.

[11] Patent Number: 5,351,686
[45] Date of Patent: Oct. 4, 1994

[54] DISPOSABLE EXTRACORPOREAL CONDUIT FOR BLOOD CONSTITUENT MONITORING

[75] Inventors: Robert R. Steuer, Pleasant View; David H. Harris, Ogden, both of Utah

[73] Assignee: In-Line Diagnostics Corporation, Ogden, Utah

[21] Appl. No.: 66,344

[22] Filed: May 24, 1993

Related U.S. Application Data

[63] Continuation-in-part of Ser. No. 11,882, Feb. 1, 1993, which is a continuation of Ser. No. 598,169, Oct. 6, 1990, abandoned.

[51] Int. Cl.$^5$ .............................................. A61B 5/00
[52] U.S. Cl. ................................. 128/633; 128/637; 128/664; 128/665; 128/667
[58] Field of Search ...................... 128/632–634, 128/637, 664–667, 673, 675, 748; 356/39–41

[56] References Cited

U.S. PATENT DOCUMENTS

| | | | |
|---|---|---|---|
| 3,638,640 | 2/1972 | Shaw | 128/633 |
| 3,880,151 | 4/1975 | Nilsson et al. | 128/673 |
| 4,266,554 | 5/1981 | Hamaguri | 128/633 |
| 4,446,871 | 5/1984 | Imura | 128/633 |
| 4,653,498 | 3/1987 | New et al. | 128/633 |
| 4,685,464 | 8/1987 | Goldberger et al. | 128/633 |
| 4,770,179 | 9/1988 | New et al. | 128/633 |
| 4,805,623 | 2/1989 | Jöbsis | 128/633 |
| 4,825,872 | 5/1989 | Tan et al. | 128/633 |
| 4,825,879 | 5/1989 | Tan et al. | 128/633 |
| 4,832,484 | 5/1989 | Aoyagi et al. | 356/41 |
| 4,920,972 | 5/1990 | Frank et al. | 128/675 |
| 4,925,299 | 5/1990 | Meisberger et al. | 356/40 |
| 5,054,487 | 10/1991 | Clarke | 128/633 |
| 5,066,859 | 11/1991 | Karkar et al. | 128/633 X |
| 5,101,825 | 4/1992 | Gravenstein et al. | 128/633 |
| 5,111,817 | 5/1992 | Clark et al. | 128/633 |
| 5,158,091 | 10/1992 | Butterfield et al. | 128/748 X |
| 5,237,999 | 8/1993 | von Berg | 128/673 |

OTHER PUBLICATIONS

J. P. Payne and J. W. Severinghaus, Eds., *Pulse Oximetry*, Chapters 1 and 2 (1986).

*Primary Examiner*—Angela D. Sykes
*Attorney, Agent, or Firm*—Workman, Nydegger & Jensen

[57] ABSTRACT

A disposable cuvette through which to pass pulsatile flowing blood. The cuvette has a conduit with two opposed walls having a predetermined separation therebetween that varies with each pulse of the flowing blood. A sealed air pocket damps the variation of the predetermined separation. The conduit is comprised of materials which permit passage therethrough of wavelengths of selected electromagnetic radiation. The radiation is emitted from a photoemitter which, and after passing through the cuvette, is detected by a photodetector. The quantities of detected radiation are operated on by a computer which uses a spectrophotometry technique to derive therefrom a blood constituent concentration value. Preferably, both cuvette and spectrophotometry technique are used during hemodialysis to derive changes in the hematocrit value of the blood of a dialyzed patient, thereby to deduce therefrom changes in the blood volume of the patient during dialysis. The technique enables a clinician to monitor a desired biologic constituent concentration value, such as the hematocrit, oxygen saturation, or oxygen content values by deriving and displaying the same as digital values in real time.

53 Claims, 10 Drawing Sheets

DISPOSABLE EXTRACORPOREAL CONDUIT FOR BLOOD CONSTITUENT MONITORING

RELATED APPLICATIONS

This patent application is a continuation-in-part of U.S. patent application Ser. No. 08/011,882, filed on Feb. 1, 1993, which is a continuation of U.S. patent application Ser. No. 07/598,169, filed on Oct. 6, 1990, now abandoned.

BACKGROUND

1. Field of the Invention

This present invention is directed to an apparatus and system for deriving a desired biologic constituent concentration value present in a pulsatile flowing fluid, and is more particularly directly to such derivations in pulsatile flowing blood in a hemodialysis environment.

2. Background Art

Kidneys are located on either side of the spine. In a healthy patient, kidneys function to stimulate red blood cell production and regulate the content of the blood. Kidneys also produce hormones that affect other organs and control growth. When functioning properly, kidneys serve as a means for cleaning the blood by removing excess fluids and toxins. The filtering task in each kidney is performed in part by the some one million nephrons in the kidney. The nephrons are filtering units made up of tiny blood vessels. Each such blood vessel is called a glomerulus. Every day, roughly 200 quarts of blood and fluids will be processed by the kidney. The kidney removes about two quarts of water and toxic chemicals which are sent to the bladder as urine for subsequent voiding thereof by urination.

A patient whose kidneys are performing substandardly may be dialyzed as a substitute for the blood cleansing function normally performed by properly functioning kidneys. Dialysis is a process by which the function of the kidney of cleaning blood is substitutionarily performed. The process of dialysis was perfected for routine use in the 1960's, having been invented some 50 years ago. For the purposes of discussion and illustration of hemodialysis, FIG. 1 is now referred to. While FIG. 1 incorporates a view of a presently preferred embodiment of the present invention, it also incorporates a view of some common components which are typical in a general hemodialysis environment. The general environment of hemodialysis and typical components therein will now be discussed.

In hemodialysis, blood is taken out of a patient 200 by an intake catheter means, one example of which is shown in FIG. 1 as an input catheter 122. Input catheter 122 is intravenously inserted into patient 200 at a site 180 and is used for defining a blood passageway upstream of a blood filter used to filter the impurities out of the blood. The blood filter is also called a dialyzer 130. The unclean blood flows from an artery in patient 200 to a pump means, an example of which is pump 140. From pump 140, the blood flows to dialyzer 130. Dialyzer 130 has an input port 230 and an output port 240. The pump 140 performs the function of moving the unclean blood from patient 200 into input port 230, through dialyzer 130, and out of dialyzer 130 at output port 240.

Specifically, unclean blood in input catheter 122 is transported to input port 230 of dialyzer 130. After passing through and being cleansed by dialyzer 130, the blood may receive further processing, such a heparin drip, in hemodialysis related component 300. The now clean blood is returned to patient 200 after the dialyzing process by means of an output catheter means, an example of which is output catheter 124. Output catheter 124, which is also intravenously inserted into patient 200 at site 180, defines a blood passageway which is downstream from dialyzer 130, taking the blood output by dialyzer 130 back to patient 200.

As mentioned, the hemodialysis process uses a blood filter or dialyzer 130 to clean the blood of patient 200. As blood passes through dialyzer 130, it travels in straw-like tubes (not shown) within dialyzer 130 which serve as membrane passageways for the unclean blood. The straw-like tubes remove poisons and excess fluids through a process of diffusion. An example of excess fluid in unclean blood is water and an example of poisons in unclean blood are blood urea nitrogen (BUN) and potassium.

The excess fluids and poisons are removed by a clean dialysate liquid fluid, which is a solution of chemicals and water. Clean dialysate enters dialyzer 130 at an input tube 210 from a combined controller and tank 170. The dialysate surrounds the straw-like tubes in dialyzer 130 as the dialysate flows down through dialyzer 130. The clean dialysate picks up the excess fluids and poisons passing through the straw-like tubes, by diffusion, and then returns the excess fluids and poisons with the dialysate out of dialyzer 130 via an output tube 220, thus cleansing the blood. Dialysate exiting at output tube 220 after cleansing the blood may be discarded.

In sum, unclean blood flows from an artery in patient 200 to pump 140 and then to dialyzer 130. Unclean blood flows into dialyzer 130 from input catheter 122 and clean blood flows out of dialyzer 130 via output catheter 124 back to patient 200.

Hemodialysis, which removes excess fluids from the blood of a patient, has an acute impact on the fluid balance of the body due in part to the rapid change in circulating blood volume. When the fluid removal rate is more rapid than the plasma refilling rate of the body, the intravascular blood volume decreases. This resulting fluid imbalance has been linked to complications such as hypotension, loss of consciousness, headaches, vomiting, dizziness and cramps experienced by the patient, both during and after dialysis treatments. With hypotension and frank shock occurring in as many as 25% of hemodialysis treatments, dialysis induced hypovolemia remains a major complication of hemodialysis.

Many dialysis patients already have compromised circulatory responses due to the secondary effects of the end stage renal disease. A malfunctioning of the blood pressure compensatory mechanisms due to intravascular volume depletion has been considered to be one of the major factors causing dialysis induced hypotension.

In order to reduce the chance of dialysis induced hypotension, continuous measurement of the circulating blood volume can optimize dialysis therapy regimes, control the fluid balance, and aid in achieving the dry weight goal of the patient on a quantitative basis. Volumetric controllers, while giving a precise measurement of the amount of fluid removed through ultrafiltration, do not give any indication of how the plasma refilling mechanisms of the body are responding to the actual fluid removal. Factors such as food and water intake and postural changes also significantly effect the circulating blood volume during dialysis. Maneuvers such as eating, drinking and posture, illustrate how sensitive the plasma refilling mechanisms are.

The hematocrit value gives an indication of blood volume change. Since the number of red blood cells in whole blood is not significantly altered by dialysis, and the mean corpuscular volume of the red cells remains essentially constant, it follows that the changes in blood volume will be inversely proportional to the changes in hematocrit. Therefore, blood volume change of the patient may be defined at any time during the course of dialysis treatment as in EQUATION 1.

$$\frac{BV_{final}}{BV_{initial}} = \frac{Hct_{initial}}{Hct_{final}} \qquad \text{EQUATION 1}$$

Where:

$BV_{final}$ = Final Blood Volume
$BV_{initial}$ = Initial Blood Volume
$HCT_{final}$ = Final Hematocrit Value In the clinical setting, however, it may be more useful to determine the percentage of blood volume change as represented by EQUATION 2.

$$100\% \times \frac{BV_f - BV_i}{BV_i} = \left[ \frac{Hct_i}{Hct_f} - 1 \right] \times 100 \qquad \text{EQUATION 2}$$

Where:

$BV_f$ = Final Blood Volume
$BV_i$ = Initial Blood Volume
$HCT_i$ = Initial Hematocrit Value
$HCT_f$ = Final Hematocrit Value It is known to use hematocrit change as a measure of the actual blood volume change occurring during dialysis. However, in order that the relationship between hematocrit change and blood volume change to be useful, the hematocrit must be monitored accurately, continuously and in real time during the entire hemodialysis treatment session. While accuracy may be achieved through elaborate technical means, to be clinically practical, a real time hematocrit and blood volume monitor should be easy to use, save nursing staff time, operate noninvasively and be justifiable on a cost basis.

Various techniques employed to monitor intravascular blood volume change, due to ultra filtration, as a function of hematocrit value include microcentrifugation, electrical conductivity, and photometry.

In microcentrifugation, a microcentrifuge is used to measure hematocrit. This process is inadequate for monitoring real time changes in blood volume, due to the amount of time that elapses between measurements, the large potential for reader and sampling error, and the need to compensate appropriately for trapped plasma in the red cells columns. Hence, because of the labor intense nature of centrifuging the blood samples of the patient on a timely basis, this technique is wholly inadequate, impractical, and far too costly for wide scale clinical application.

In an attempt to achieve real time hematocrit information, electrical conductivity measurements have been used. Conductimetric measurements, however, are adversely affected by abnormal electrolyte, anticoagulant, and protein concentrations, all of which are prevalent among dialysis patients. Hence, this particular technique is fraught with significant technical errors as well.

Optical techniques, while generally unaffected by the above problems, have been susceptible to other instabilities. These include ambient light variations, tubing artifact, changes in blood flow rate, in-line pressures, and oxygen saturation. Additionally, the light sources used in optical techniques require frequent calibration.

BRIEF SUMMARY AND OBJECTS OF THE INVENTION

In light of the above described deficiencies in the art, it is an object of the present invention to provide a system having an optical method for noninvasively and continuously monitoring the percent blood volume change during hemodialysis.

It is another object of the present invention to monitor the percent blood volume change during hemodialysis without the instabilities, inaccuracies and need for calibration observed in presently known photometric techniques.

Another object of the present invention is to provide a hemodialysis system in which real time hematocrit and blood volume monitoring is performed.

It is still another object of the present invention that the real time hematocrit and blood volume monitoring component of the hemodialysis system be easy to use, save nursing staff time, operate noninvasively and be justifiable on a cost basis.

A further object of the present invention is that the end user, nurse, clinician, or patient may ascertain the percentage of blood volume change and a desired biologic constituent concentration digital value in the blood during hemodialysis in real time, or as a real time continuous analogue display of the value, where the constituent concentration value includes the hematocrit value, the oxygen saturation value, and the oxygen content value.

A still further object of the present invention is to provide a hemodialysis system having the multiple capabilities of monitoring simultaneous, real-time, computation and display of the hematocrit and oxygen saturation values as well as the percentage change in the blood volume in a patient undergoing hemodialysis.

An other object of the present invention is to provide a novel fluid cuvette which may be used in a spectrophotometric determination of a desired biologic constituent concentration value in a fluid passing through the novel cuvette by subjecting the cuvette, and the fluid therein, to electromagnetic radiation, and then utilizing the electromagnetic radiation passing therethrough as the constituent concentration value information carrier.

A still further object of the present invention is to provide a novel fluid cuvette which may be used in hemodialysis in conjunction with spectrophotometric real time determination of the hematocrit value of a patient undergoing hemodialysis.

An object of the present invention is to provide a novel fluid cuvette which is comprised of materials of low cost, and which is inexpensive to manufacture, such that the cuvette is economical to dispose of after use.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the invention is directed to an apparatus and a system incorporating the apparatus. The apparatus is a disposable, extracorporeal cuvette through which a fluid flowing in a pulsatile fashion passes.

The cuvette has an inlet, also called a first fluid conduit, and an outlet, also called a third fluid conduit. In between the inlet and the outlet there is a conduit, also called a second fluid conduit, that is in fluid communication with the inlet and outlet.

The conduit has two opposed walls which have a predetermined separation between them. The two opposed walls constrain at least some of the pulsatile fluid flowing through the conduit. The conduit also has a transducer means which is located in one of the opposed walls. The transducer means varies the predetermined separation between the two opposed walls in response to pressure pulsations in the pulsatile flowing fluid.

The conduit may alternatively be stated as having a means, in contact with the pulsatile flowing fluid therein, for making a resilient fluctuation with each pulse of the pulsatile flowing fluid in the conduit. The resilient fluctuation is made in a direction that is essentially normal or perpendicular to the general direction of movement of the pulsatile fluid that is flowing in the conduit. The resilient nature of the fluctuation means ensures its return to its original position after it makes the fluctuation.

The conduit, also called the second fluid conduit, is comprised of materials which permit at least two predetermined wavelengths of electromagnetic radiation, and preferably four wavelengths, to transmissively pass therethrough. The materials used are preferably low cost so that the cuvette is economical both to dispose of after use and to manufacture.

It is intended herein that the term "fluid" means alternatively liquid or gaseous substances. It is also intended herein that "pulsatile" is meant to be rhythmical or cyclical surges or pressure increases in a fluid flowing under pressure.

The system incorporating the cuvette is designed for monitoring the concentration of a particular or desired biologic constituent. Preferably, the pulsatile flowing fluid is blood of a patient and the desired biologic constituent concentration being monitored in the system is the red blood cell concentration, also expressed as the hematocrit value. The preferable system in which the constituent concentration monitoring takes place is a hemodialysis system where the hematocrit value is monitored, both before and after the blood cleansing process, as a means of deriving the blood volume change during the hemodialysis process.

The constituent concentration monitoring calculations are performed using the technique disclosed in U.S. patent application Ser. No. 08/011,882, filed on Feb. 1, 1993, and titled "SYSTEM AND METHOD FOR NONINVASIVE HEMATOCRIT MONITORING," which is hereby incorporated by reference, and is hereinafter referred to as The Incorporated Technique.

The constituent concentration calculations, disclosed in The Incorporated Technique, are performed upon data derived by passing multiple wavelengths of light through the extracorporeal blood conduit or a body part of a patient. Means are also disclosed and provided by The Incorporated Technique for delivering and detecting these multiple wavelengths of light and for analyzing the various detected light intensities. The spatial arrangement for both sensing and for emitting the light is detailed so as to give the optimum repeatability of the signals and data derived therefrom. Finally, memory and calculation means are included which are capable of storing, manipulating, displaying, and printing out the detected signals in a variety of ways. The Incorporated Technique enables an end user, nurse, clinician, or patient to ascertain a desired biologic constituent concentration value, such as the hematocrit value, the oxygen saturation value, or the oxygen content value by displaying the same as digital values in real time.

While the apparatus of the present invention is preferably applicable in the area of kidney dialysis, it may also be employed in cardiovascular surgery or in other medical fields where blood is present in extracorporeal tubing. In these environments, the present invention derives the blood hematocrit value, the blood oxygen saturation, the blood oxygen content, and the change in blood volume. These derivations are all made, via the present invention, without the need of an invasively obtained stagnant blood sample. Advantageously, the derivation of the hematocrit value in such cases provides repeatable and reliable determinations, noninvasively and continuously, of the hematocrit value of a patient independent of the status of perfusion or cardiac output of the patient.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in tile appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENTS

The present invention contemplates a system and an apparatus therein for determining the concentration of a biologic constituent that is present in the blood of a patient undergoing hemodialysis treatment.

1. The System

Figure 1:
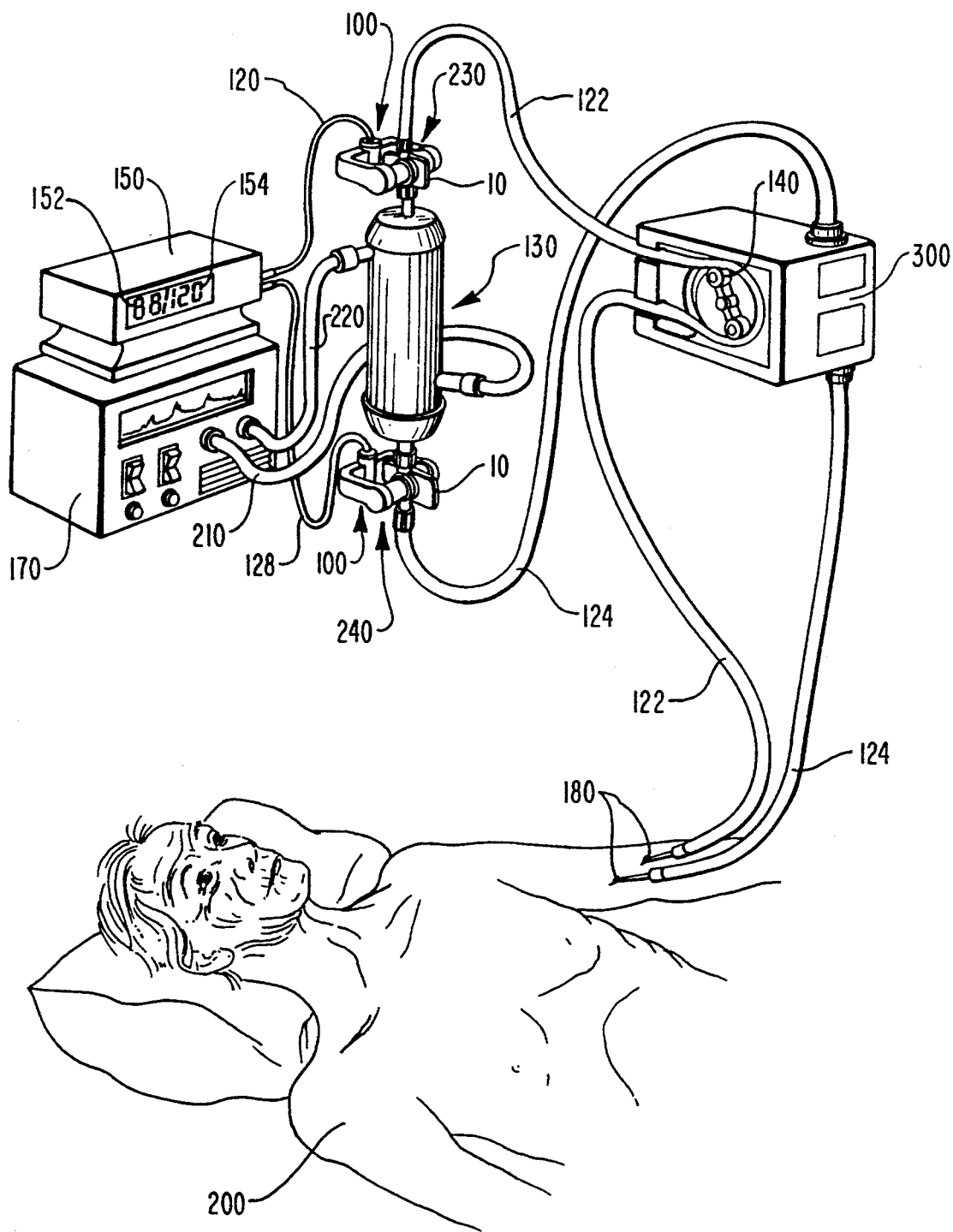
FIG. 1 is an environment view of a patient undergoing hemodialysis treatment and shows a system incorporating principles of a presently preferred embodiment of the invention, including a pair of cuvettes having thereon spectrophotometry components.

The general hemodialysis process and environment is seen in FIG. 1 and has been described above. A summary of this process is that patient 200, whose kidneys are performing substandardly, is dialyzed. The unclean blood flows from an artery in patient 200 to the 140 and then to dialyzer 130. Unclean blood flows into dialyzer 130 from input catheter 122, and then clean blood flows out of dialyzer 130 via output catheter 124 back to patient 200.

It is preferable that the pump 140 causes the blood flowing into, through, and out of dialyzer 130 to flow in a pulsatile fashion.

Installed at either end of dialyzer 130 is a spectrophotometry means for defining a blood flow path, for emitting radiation into the blood in the flow path, and for detecting radiation passing through both the blood and the flow path. The spectrophotometry means includes a cuvette means for defining the blood flow path, and an emitter/detector means for directing and detecting radiation. Within the emitter/detector means is both an emission means for directing radiation and a detector means for detecting radiation.

Figure 3:
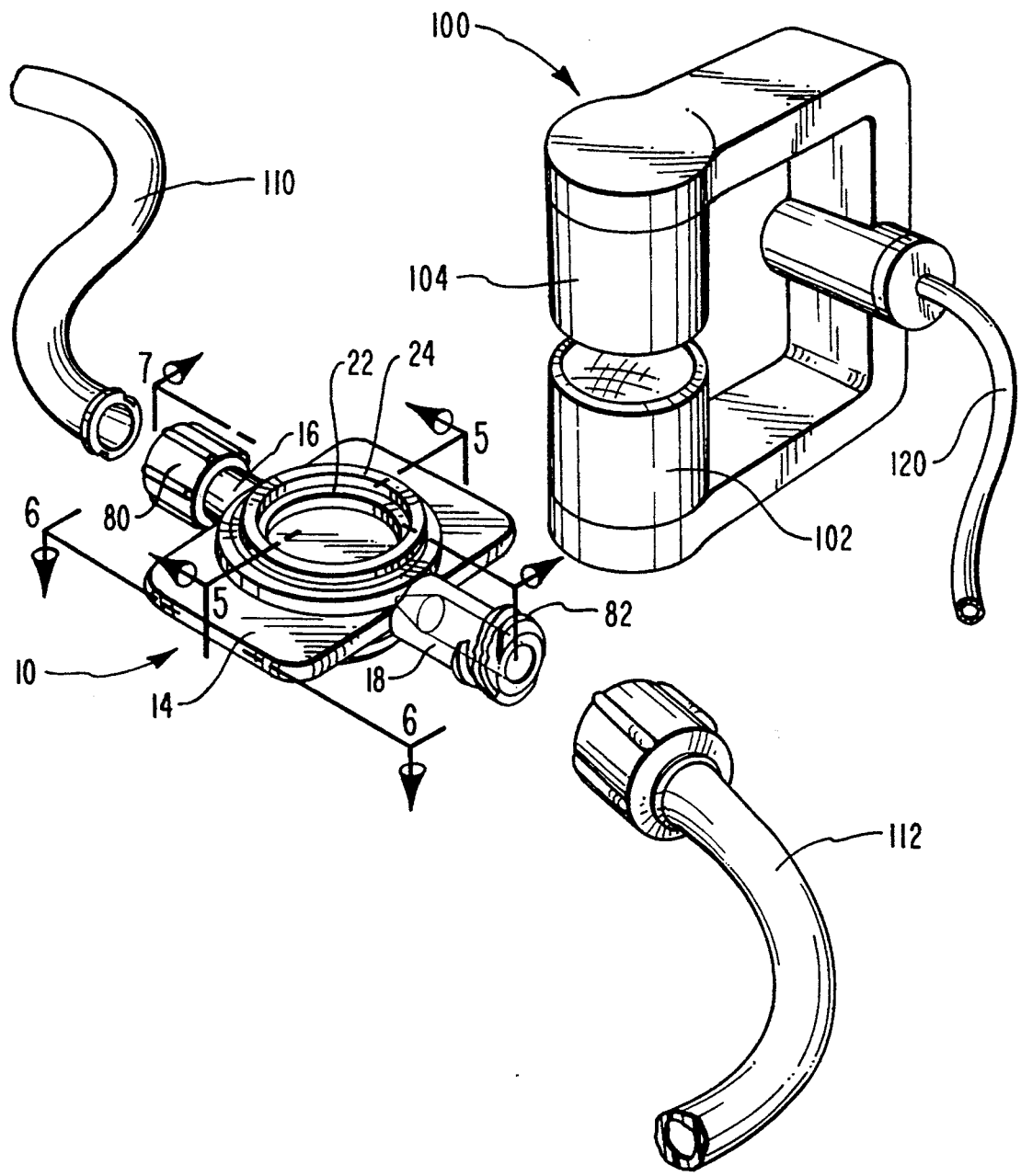
FIG. 3 is a perspective view of FIG. 2 with the various components thereof disconnected.
Figure 8:
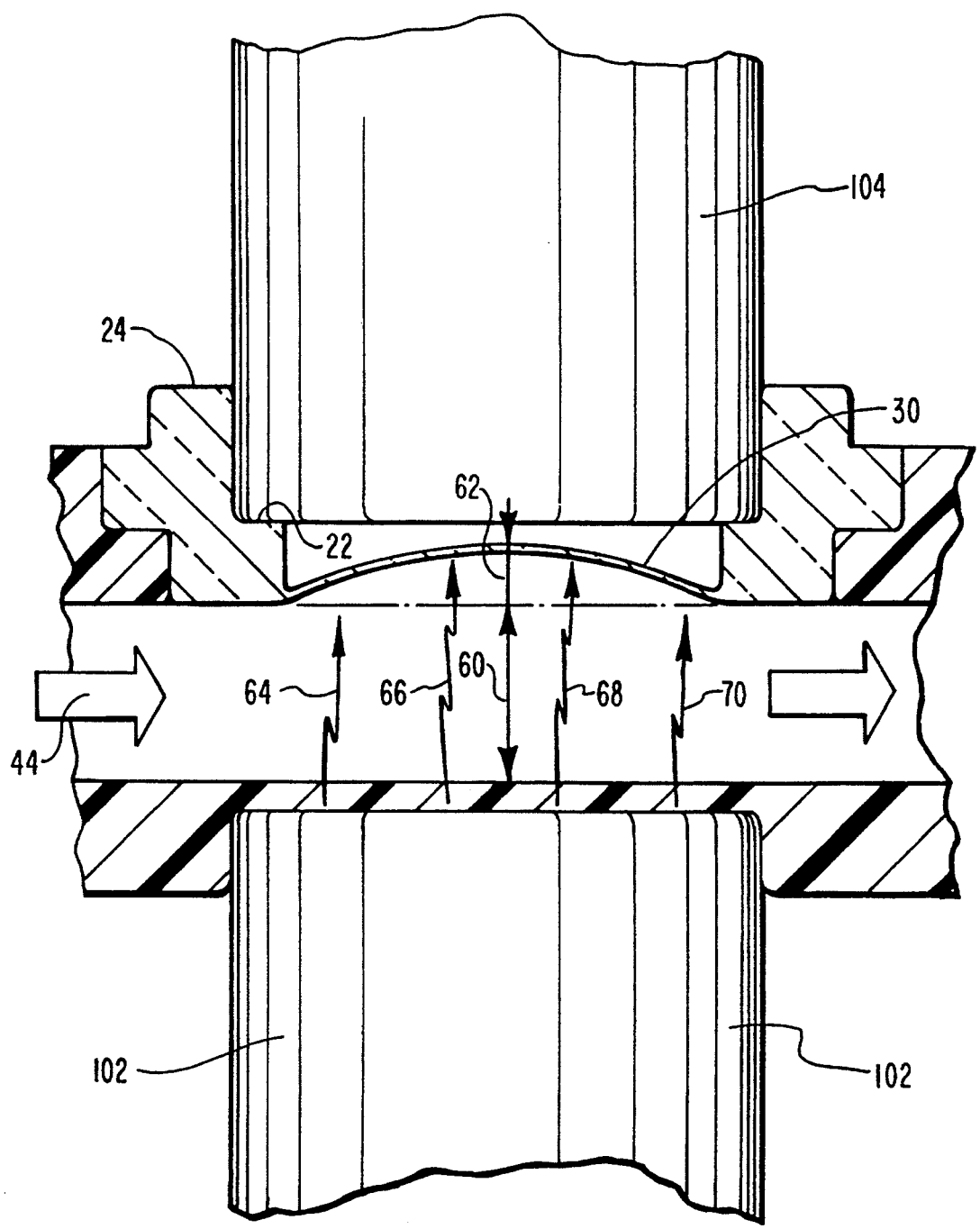
FIG. 8 is a cut-away cross-sectional view, taken-along Section Line 8—8 of FIG. 2, depicting radiation at four (4) wavelengths directed towards a flexible wall within the cuvette.

In the preferred embodiment, as shown in FIGS. 3 and 8, an example of the emitter/detector means is depicted by the emitter/detector apparatus 100. An example of the emission means is indicated by a photoemitter 102. Emitter/detector apparatus 100 also has a detection means, an example of which is depicted as a photodetector 104. An example of the cuvette means is shown in FIGS. 3 and 8 as cuvette 10.

Emitter/detector apparatus 100 enables the detection by photodetector 104 of the portion of radiation which is directed by photoemitter 102 to cuvette 10 and passes through both the blood therein and cuvette 10.

Figure 2:
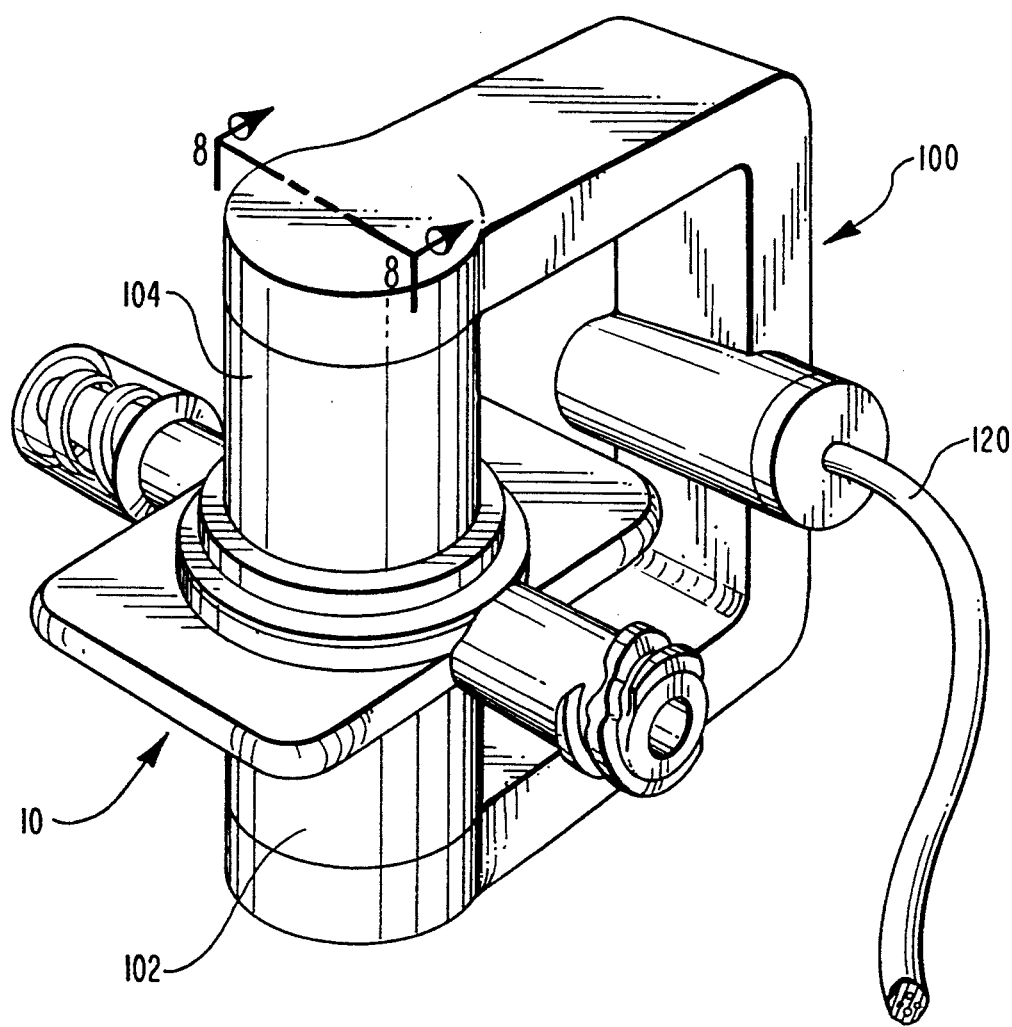
FIG. 2 is an enlarged cut-away perspective view of a cuvette shown in FIG. 1.

As shown in FIGS. 2 and 8, a cuvette 10 is installed at either end of dialyzer 130. Each cuvette 10 has a photoemitter 102 and a photodetector 104 thereon. In the preferred embodiment of the system, photoemitter 102 and photodetector 104 are shown as being held together by a spring-loaded C-Clamp type in emitter/detector photo apparatus 100.

The emitter/detector means is electrically connected to a calculation means. In a preferred embodiment of the system, an example of the calculator means is depicted in FIG. 1 as computer 150 which is electrically connected to photoemitter 102 and photodetector 104 on emitter/detector apparatus 100 by means of cable 120.

Intake catheter 122 takes blood to cuvette 10 situated before input port 230 of dialyzer 130. Emitter/detector apparatus 100 at input port 230 of dialyzer 130 subjects the blood therein to at least two radiation wavelengths of electromagnetic radiation for the purposes of analysis, via spectrophotometry, so that the concentration of a desired biological constituent can be derived. Each photodetector 104, at both input port 230 and output port 240 of the dialyzer 130, communicates the detected radiation at least a first and a second wavelength via cable 120 to computer 150.

Computer 150 calculates both before dialysis and after dialysis concentrations of the sought-after or desired biologic constituent. Computer 150 then displays, respectively, at a first display 152 and a second display 154, the derived concentration of the biological constituent in either analogue or digital representations. The calculation means, shown here by example as computer 150, preferably has the multiple capability of simultaneous real-time computation and display of the hematocrit and oxygen saturation values as well as the percentage change in the blood volume in a patient undergoing hemodialysis.

The choice and predetermination of radiation wavelengths is based upon the desired biologic constituent for which the concentration value is sought. Photoemitter 102 preferably emits, and photodetector 104 preferably detects, four (4) predetermined wavelengths for the spectrophotometry techniques taught in The Incorporated Technique. Accordingly, cuvette 10 preferably will be comprised of materials that permit the four (4) predetermined wavelengths of directed radiation to pass therethrough.

2. The Apparatus a) A Preferred Embodiment

In the presently preferred embodiment, an example of the cuvette means is the disposable fluid cuvette 10 in FIGS. 1 through 8. The inlet and the outlet to the cuvette are respectively indicated at 16 and 18, between which lies a cylindrical shaped portion of the cuvette 10, called herein the conduit, or alternatively the second fluid conduit.

Figure 4:
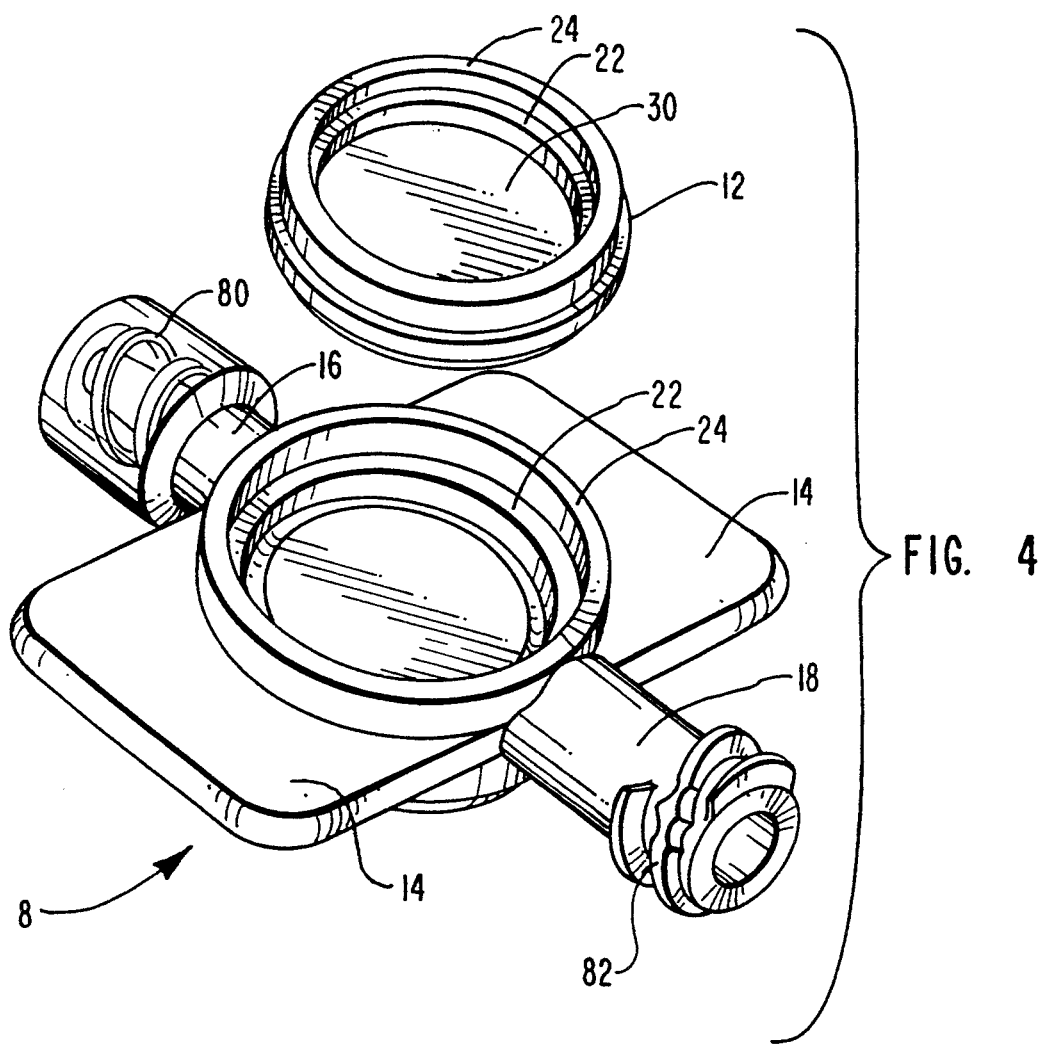
FIG. 4 is an exploded view of the cuvette shown in FIG. 3.
Figure 5:
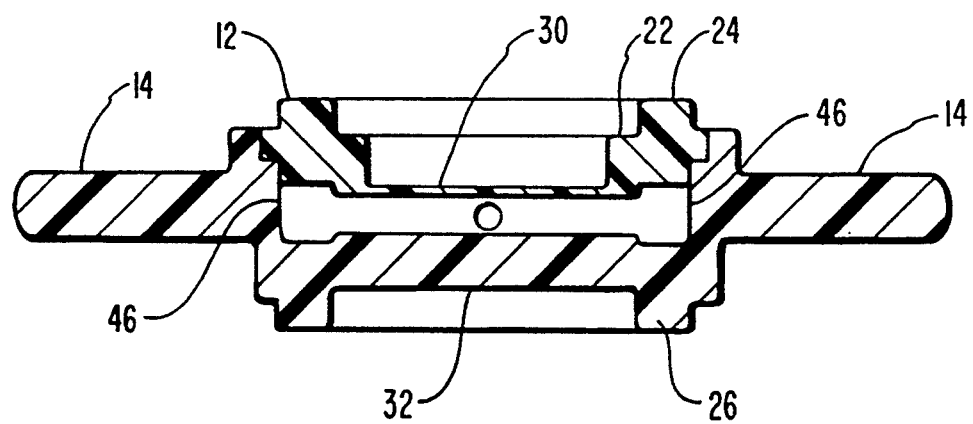
FIG. 5 is a cross-sectional view taken-along the Section Line 5—5 of FIG. 3.
Figure 6:
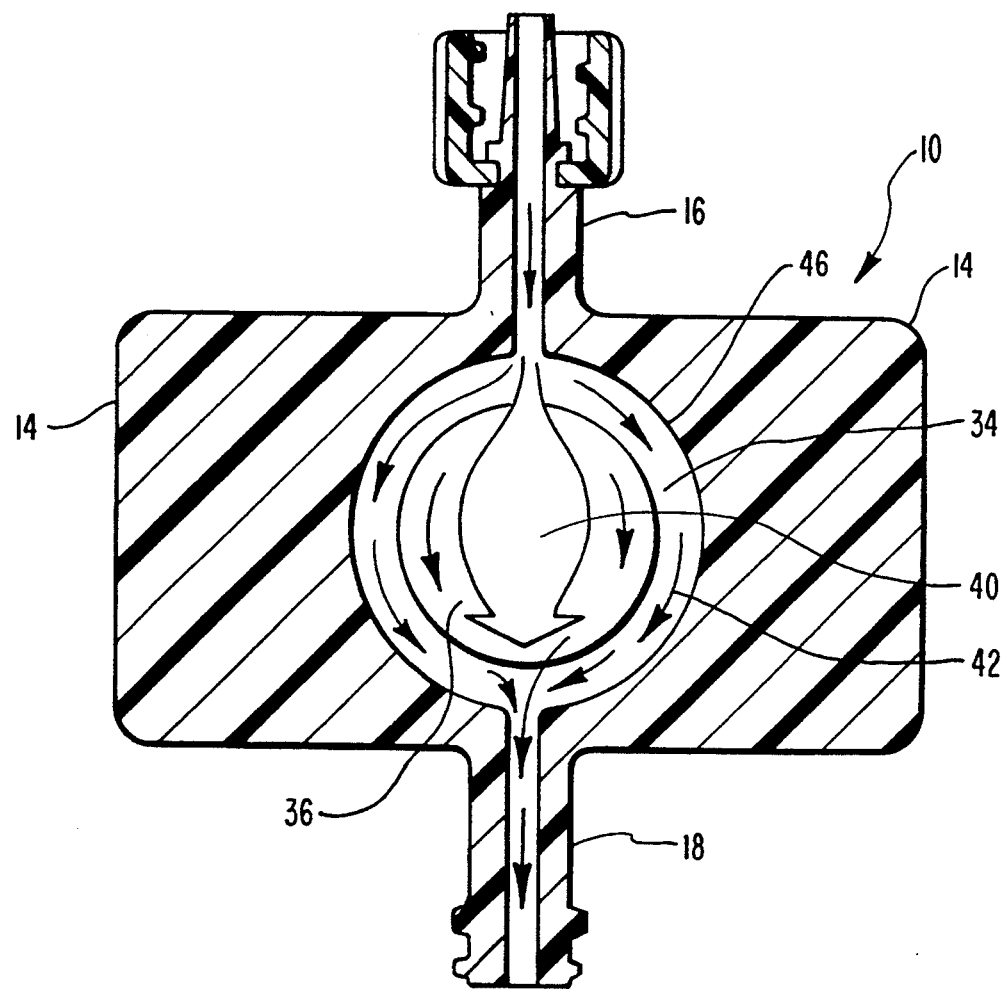
FIG. 6 is a cross-sectional view, taken-along Section Line 6—6 of FIG. 3, showing fluid flow paths within the cuvette.
Figure 7:
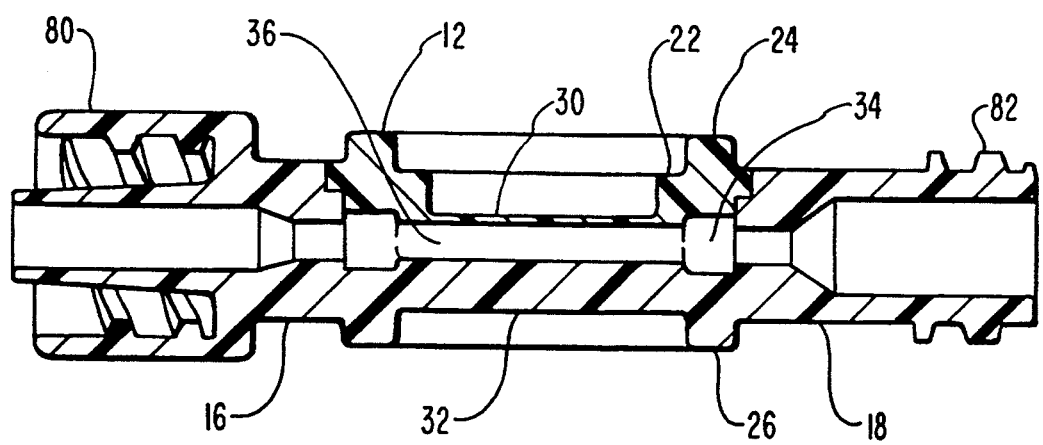
FIG. 7 is a cross-sectional view, taken-along Section Line 7—7 of FIG. 3.

As shown in FIG. 4, there is an upper housing assembly 12 which is assembled into lower housing assembly 8 so as to form cuvette 10. Upper housing assembly 12 can be installed to lower housing assembly 8 by means of an adhesive. Other and equivalent means such as friction welding or ultrasonic welding can also be employed. The purpose in properly sealing upper housing 12 to lower housing 8 is to create therebetween a fluid impervious and sealed attachment so that fluids conducted through cuvette 10 will not leak, seep, or wick-up at the points of connection between upper housing 12 and lower housing 8. The lower housing 8 has hand holds or wings 14 by which the cuvette 10 may be manually handled.

The conduit incorporates a transducer means. As stated, the transducer means varies the predetermined separation between the two opposed walls with each pressure pulsation in the fluid. In the presently preferred embodiment, an example of the transducer means is represented in FIGS. 4, 5, 7 and 8 as wall 30 which has an opposing wall 32 thereto.

Figure 12:
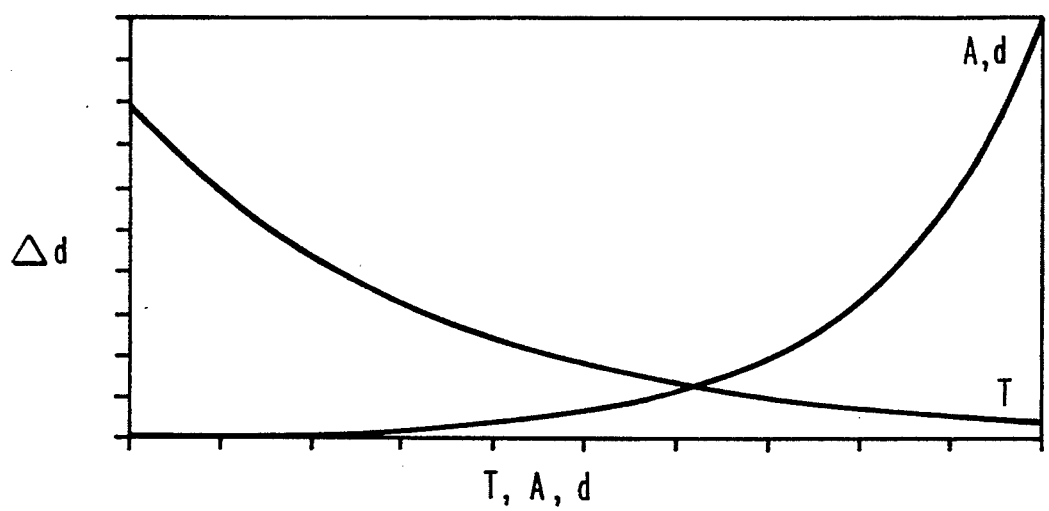
FIG. 12 depicts the physical variable relationships between the component dimensions of the cuvette shown in FIG. 8, including the blood layer thickness and changes therein (d and $\Delta d$, respectively), the disposable membrane thickness (T), and the area of the membrane (A).

The pulsatile flowing fluid flows in the conduit within the area bounded in between a vertical wall 46 and opposed walls 30 and 32. The fluid within the conduit assumes the flow paths indicated by arrows 40 and 42 in FIG. 6. The flow path seen in FIG. 8 at 44, which describes fluid flow as it enters at inlet 16 into the conduit, will assume flow path 40 within area 36 or, alternatively, will assume flow path 42 within area 34. The fluid flowing between opposed walls 30 and 32 is described by the area marked as 36. FIG. 12 depicts the area 36 as 'A'. The fluid flowing outside of opposed walls 30 and 32 flows in the direction indicated by arrow 42 in the area marked as 34 in FIGS. 6 and 7. The fluid volume in area 34 is preferably greater than that of area 36.

Inlet 16 and outlet 18 are linearly aligned on either side of the conduit and share a common longitudinal axis passing therebetween. The cylindrical conduit between inlet 16 and outlet 18 has a longitudinal axis passing through opposing walls 30, 32 that is normal to the common longitudinal axis of inlet 16 and outlet 18. FIG. 12 depicts wall 30 as the membrane thickness 'T'. As shown in FIG. 8, opposing wall 30 is preferably thinner than opposing wall 32.

As fluid in flow path 44 makes a pressure pulsation surge, opposing wall 30 flexes into an arcuate shape while opposing wall 32 remains relatively immobile. The deformation in wall 30 is depicted by flex line 62 seen in FIG. 8. After the pressure pulsation of fluid in flow path 44, the wall 30 returns to the position shown in phantom such that the separation between wall 30 and 32 is indicated by distance 60. The relationship between the distance 60 and flex line 62 is graphically depicted in FIG. 10, respectively by d and Δd.

As mentioned, wall 30 is an example of the transducer means. Other equivalently functioning transducer means could be incorporated into the conduit such that the distance, shown by line 60 in FIG. 8, between opposing walls 30 and 32 could be varied. By way of example, and not by way of limitation, the transducer means could be constructed essentially of silicone. Alternatively, a small section of opposing wall 30 could be made to vary the distance between the opposed walls 30, 32. Such a portion may be spring-loaded or have other resilient means for returning the small section of wall 30 to its original pre-pulse lower pressure position. In such an embodiment, the opposing wall 30 need not be thinner than opposing wall 32.

FIG. 8 depicts optical paths 64, 66, 68, and 70 of directed electromagnetic radiation at four (4) different wavelengths. Each wavelength is selected for spectrophotometric compatibility with a specific biologic constituent in the pulsatile flowing fluid. As described, the detected portion of the directed radiation is used to derive the concentration value using The Incorporated Technique. Wavelengths may be fixed in emitter/detector apparatus 100 or may be set by adjusting the computer 150, where the photoemitter 102 and the photodetector 104 are dynamically adjustable as to wavelength at computer 150.

The opposing wall in the conduit which incorporates the transducer means also has a means for receiving an emission means that extends from the wall. The other of the opposed walls has a means for receiving a detector means. In the presently preferred embodiment, the means for receiving a photoemitter is indicated in FIGS. 3, 4, 5, and 7 as the combination of a first ring-shaped surface 22 with a second ring-shaped surface 24, both of which extend from opposing wall 30. The two ring-shaped surfaces 22 and 24 are styled to accept cylindrical photoemitter 102, shown in FIGS. 2, 3, and 8.

A means extends from the other one of the opposed walls for receiving a detector means. In the presently preferred embodiment, the ring-shaped surface 26 is concentric to ring-shaped surfaces 22 and 24 and extends from opposing wall 32 so as to accept cylindrical photodetector 104.

As to the cuvette 10, it is preferable that ring-shaped surfaces 22 and 24 are concentric to each other and are concentric with ring-shaped surface 26, and that ring-shaped surface 22 has a lesser inner diameter than ring-shaped surface 24.

Figure 9:
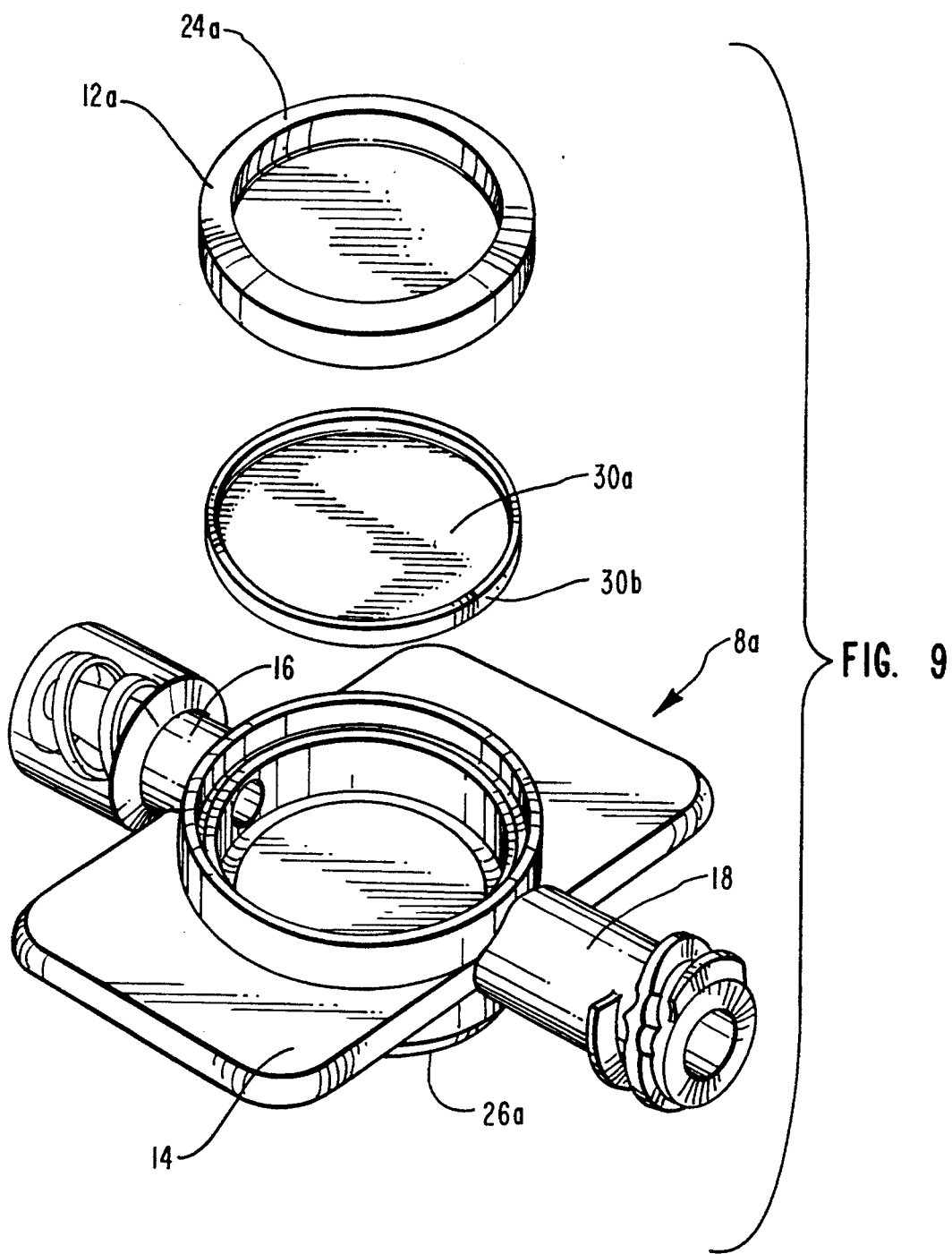
FIG. 9 is an exploded view of an alternative embodiment of the cuvette shown in FIG. 3.
Figure 10:
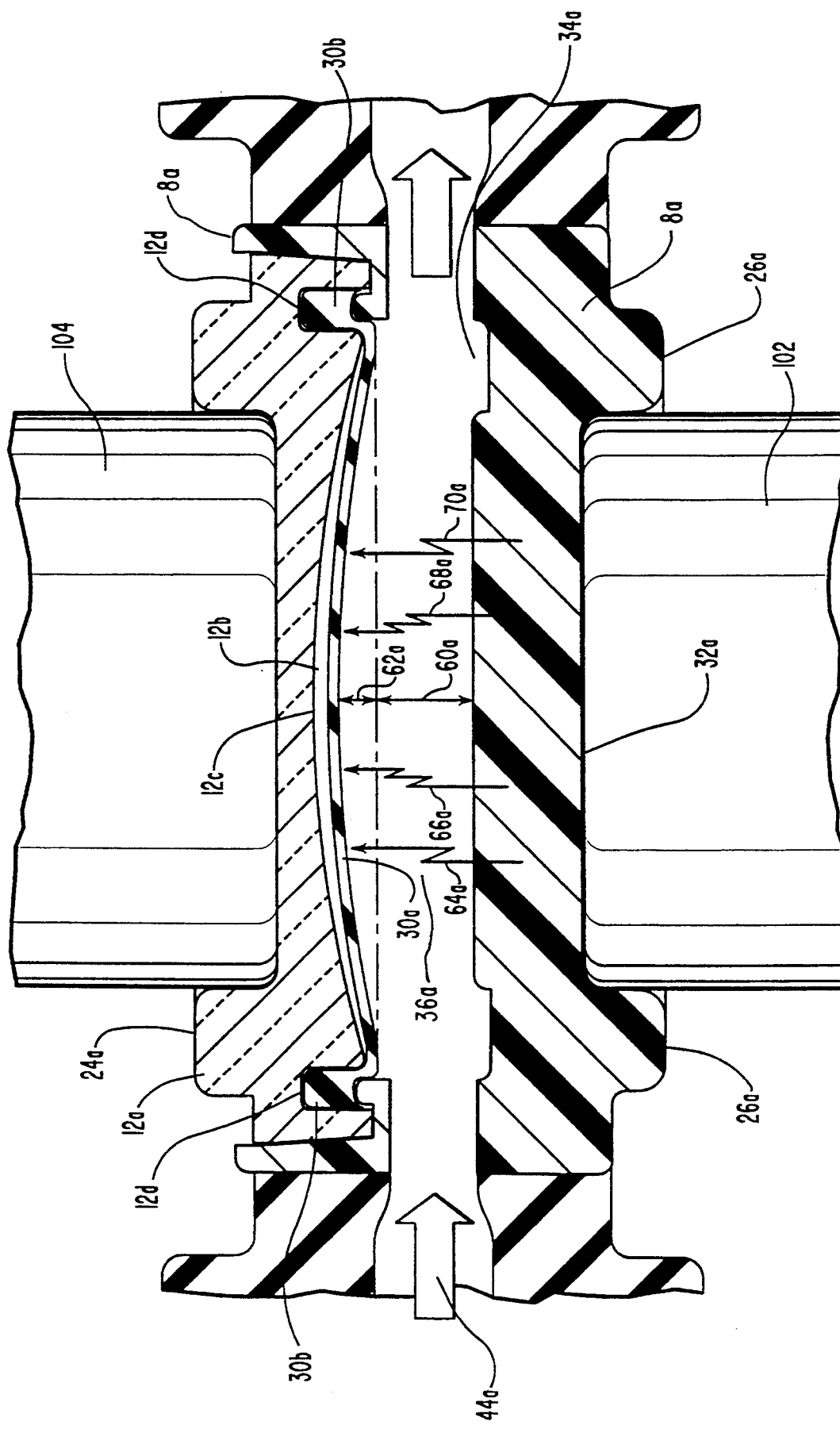
FIG. 10 is a cut-away cross-sectional view of the alternative embodiment of the cuvette, taken-along Section Line 8—8 of FIG. 2, depicting radiation at four (4) wavelengths directed towards a flexible silicone membrane within the cuvette.

An alternative embodiment of the cuvette includes means which is responsive to pressure pulsations in the fluid flowing through the conduit and which damp the variations of the predetermined separation between two opposed walls. An example of this alternative embodiment is depicted in FIGS. 9 and 10 in which the flex of a membrane or diaphragm 30a is damped by air pocket 12b.

Diaphragm 30a may be comprised of silicone having a preferred thickness of 0.020 inches, or of either PVC or PETG having a preferred thickness of 0.005 inches. Other silicone-like diaphragms, with appropriate thickness, are also capable of performing equivalently and as such are considered equivalents. Diaphragm 30a has a circular periphery 30b which is wedged into a housing 12a and lower housing 8a, both of which are preferably comprised of medical grade plastic, sandwich the silicone diaphragm 30a therebetween.

Upper housing 12a has a convex surface 12c facing both wall 32a and silicone membrane 30a. The convex surface 12c is a side of a third wall, where silicone membrane 30a and wall 32a form the first and second walls.

Blood flows circularly in area 34a and semi-linearly in area 36a. As the blood pulses, silicone membrane 30a flexes from distance 60a by an increment of 62a, while wall 32a and surface 12c are relatively immobile. The silicone membrane 30a is an example of a transducer which varies the predetermined separation thickness of the blood flow path in the conduit with each pressure pulsation. The presence of air pocket 12b will damp the flex of silicone membrane 30a. The damping effect lessens snapping movements of the membrane 30a as it is moved by pressure pulsations in the fluid.

Air pocket 12b is preferably hermetically sealed by forming an air tight connection between lower housing 8a, upper housing 12a and the silicone membrane circular periphery 30b.

Air pocket 12b and diaphragm 30a in upper housing 12a, in an alternative embodiment not illustrated in the Figures, may be complemented by an opposite and symmetrically situated second air pocket (not shown) and second flexible diaphragm (not shown) in lower housing 8a so that the conduit has two flexible diaphragms and two air pockets. The second air pocket would be formed in an impression in wall 32a over which the second flexible diaphragm lies in like fashion that FIG. 10 depicts the arrangement of flexible diaphragm 30a and air pocket 12b in wall 12c. In such an alternative embodiment of the inventive cuvette, the blood flows in contact with and between the two flexible membranes. Pulsatile pressures in the flowing blood cause both of the flexible diaphragms to flex. The flex in each of the two flexible diaphragms are cushioned by their respective air pockets.

As a another and alternative embodiment of the inventive cuvette, the conduit has the single flexible diaphragm 30a and single air pocket 12b as depicted in FIG. 10, and also features a modification of rigid wall 32a to have a plurality of small holes or micro-striations in its surface interior to the conduit so that the holes are in contact with the blood flowing through the conduit. The holes, being of relatively small diameter, are virtually impervious to blood flowing through the conduit, yet serve to cushion the force and absorb some of the pulse pressure in the pulsatile flowing blood. The air cushioning in the micro-striations decrease the flex distance 62a and reduce both the acceleration and velocity of the flexible diaphragm 30a as it moves between its extreme positions at distance 60a and distance 62a.

In the foregoing two alternative and unillustrated embodiments, the additional air cushioning in the inventive cuvette serves to further increase the accuracy of the spectrophotometry readings by reducing the flexible diaphragm snap and flutter motion during blood pulsatile cycles.

Ring shaped surfaces 24a and 26a respectively extend from the third wall at surface 12c and the second wall 32a. Similar to that which is depicted in FIG. 8, wavelengths 64a, 66a, 68a, and 70a pass transmissively through the membrane 30a from photoemitter 102 to photodetector 104.

Air pocket 12b is preferably hermetically sealed by forming an air tight connection between lower housing 8a, upper housing 12a and the silicone membrane circular periphery 30b.

Ring shaped surfaces 24a and 26a respectively extend from the third wall at surface 12c and the second wall 32a. Similar to that which is depicted in FIG. 8, wavelengths 64a, 66a, 68a, and 70a pass transmissively through the membrane 30a from photoemitter 102 to photodetector 104.

Other means for receiving an emission means and a detector means are contemplated and need not be ring-shaped surfaces. Such means could be a structure that holds the emitter means and the detector means in close proximity to the cuvette means so as to be spatially appropriate for The Incorporated Technique.

At inlet 16 of cuvette 10 there is a luer lock connector 80 and at outlet 18 of cuvette 10 there is a luer lock connector 82. Luer lock connectors 80 and 82 are respectively connected to catheters 110 and 112. Catheters 110 and 112 are integral with the installation of cuvette 10 at input port 230 and output port 240 of dialyzer 130.

Other equivalent embodiments of the cuvette are contemplated. However, from the mathematics disclosed in The Incorporated Technique, it is clear that other embodiments of the cuvette in an extracorporeal system require a conduit wherein the blood flows unimpededly and constant. The conduit should have its dimensions balanced as to the thickness of the blood layer in the conduit (such as distance 60 in FIG. 8), the thickness of the flexible membrane in the conduit (such as wall 30 in FIG. 8), and as to the area of the flexible membrane (Such as area 36 in FIG. 6). Each of these parameters is empirically adjusted, as depicted in FIG. 12, such that the electronics as stated in The Incorporated Technique gives optimum AC pulse signals in order to use the $\Delta I/I$ in Equations B and C, below.

b) Cuvette Structural Variables

Several physical characteristics of alternative embodiments of the inventive conduit will be discussed below.

(i) The Transducer Means

Figure 11:
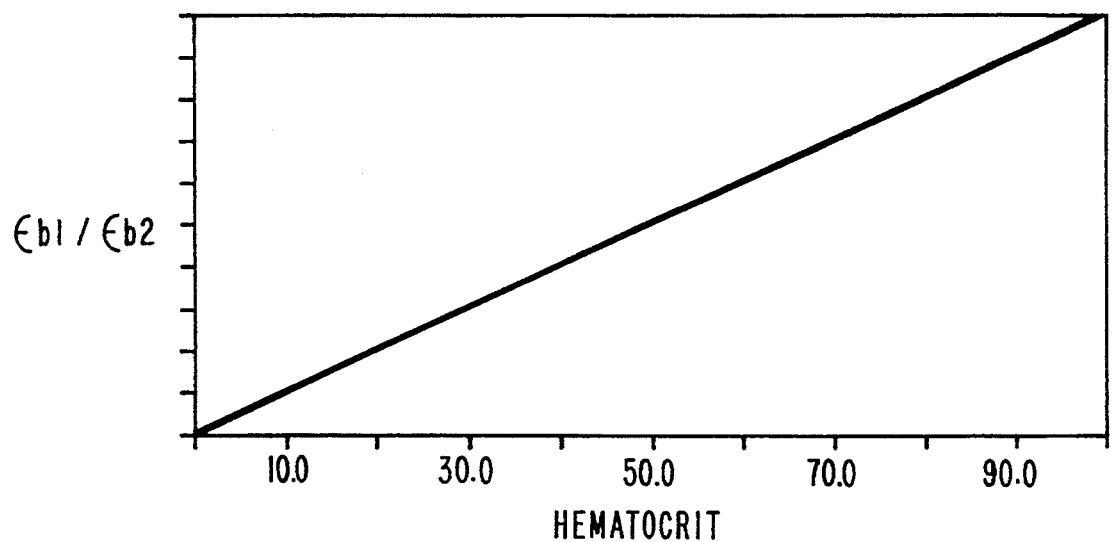
FIG. 11 is the graph of the ratio $\epsilon_{b1}/\epsilon_{b2}$ versus Hematocrit, $\epsilon_{b1}$ being the extinction coefficient of whole blood at radiation of a first radiation wavelength and $\epsilon_{b2}$ being the extinction coefficient of whole blood at radiation of a second radiation wavelength, wherein the first and second wavelengths are isobestic wavelengths such that FIG. 11 depicts a strong function of hematocrit.

The transducer means will modulate with each pump cycle of the pump means, such as pump 140 in FIG. 1, to produce a small $\Delta d$ (such as flex line 62 in FIG. 8) so that Equations A, B, and C, below, are excited into the $\epsilon_{b1}/\epsilon_{b2}$ notation (See FIG. 11, by way of example). A cursory explanation of the mathematics, more thoroughly explained in The Incorporated Technique, is as follows:

The Beer-Lambert Equation is the theoretical basis of The Incorporated Technique, as shown by EQUATION A.

EQUATION A $$I = I_o e^{-\epsilon \cdot x \cdot d + G}$$

Where:
G = Variable optical path-lengthening factor
I = Measured Intensity
$I_o$ = Incident Intensity
$\epsilon$ = Extinction Coefficient of the Media
x = Concentration of the Media
d = Thickness of the Media In a practical hemodynamic application of EQUATION A, as the blood layer d (such as distance 60 in FIG. 8) pulsates, due to a pumping means (such as pump 140 in FIG. 1), the concentration x remains constant, but the blood layer d (such as distance 60 in FIG. 8) will change by $\Delta d$ (such as flex line 62 in FIG. 8) due to the transducer means (such as wall 30 in FIG. 8). Hence, taking the partial derivatives of EQUATION A with respect to time, and then dividing EQUATION A by itself, will give EQUATION B.

$$-\frac{\partial I/\partial t}{I} = \epsilon_b \cdot x \cdot \frac{\partial d}{\partial t} \quad \text{EQUATION B}$$

Where:

$$\frac{\partial d}{\partial t} \approx \Delta d$$

$$\frac{\frac{\partial I}{\partial t}}{I} \approx \Delta I/I$$

and $\epsilon_b$ = extinction coefficient of whole blood.

In order to obtain the result in EQUATION B, G in EQUATION A is assumed to be negligible due to the fixed dimensions of the conduit.

As a practical application of EQUATION B, suppose that two wavelengths, such as 805 nm and 1300 nm, both of which are isobestic wavelengths, are now chosen, as was done in The Incorporated Technique. The Incorporated Technique calls for a ratio to be taken of EQUATION B at the first wavelength to EQUATION B at the second wavelength. Thus, the ratio of $\Delta I/I$ at wavelength 1 to the ratio $\Delta I/I$ at wavelength 2 results in the cancellation of both $\Delta d$ and x, leaving only $\epsilon_{b1}/\epsilon_{b2}$ in EQUATION C.

$$\frac{(\Delta I/I)_1}{(\Delta I/I)_2} = \frac{\epsilon_{b1}}{\epsilon_{b2}} \qquad \text{EQUATION C}$$

Where:
$\epsilon_{bn}$ = Coefficient of Extinction in whole blood at the nth wavelength; and
n = Wavelength.

The advantage of selecting these wavelengths as such is that, at these wavelengths, the ratio of the extinction coefficients, $\epsilon_{b1}/\epsilon_{b2}$, will be a strong function of hematocrit in pulsatile flowing blood passing through the cuvette. This strong function is graphically seen in FIG. 11.

The Incorporated Technique is advantageous in that several terms in the mathematics of the above equations eliminate themselves, as shown in EQUATIONS B and C, thus dramatically simplifying the determination of the concentration of a biologic constituent in the pulsatile flowing fluid. As mentioned, a principle component which is eliminated is the concentration x, which divides itself out in the ratio. Additionally, the $I_o$ term cancels out in EQUATION B, where $I_o$ is the term for the incident intensity.

(ii) Wings or Hand Holds

The wings or hand holds, such as wings 14 in FIGS. 3 through 6, are preferably thin to allow installation of the cuvette in areas where there is a tight fit necessary to facilitate connection of the same to blood tubing. The wings or hand holds also lessen the potential for fingerprints on the flexible membrane, such as wall 30 in FIG. 8.

(iii) Flow Volume in the Cuvette

The cuvette will preferably maintain adequate blood flow across the flexible membrane while allowing the major volume flow through the outer annular area, an example of which is wall 30 with flow path 40 versus vertical wall 46 and flow path 42. A construction of this arrangement prevents turbulence in the conduit, decreases the velocity immediately under the flexible membrane sensor, and reduces the sensitivity to flow rate in the conduit.

(iv) The Flexible Membrane

The flexible membrane stiffness depends on the thickness of the membrane and the area thereof. Such stiffness minimizes the absolute movement of d, which is the thickness of the blood flowing through the cuvette, such as distance 60 in FIG. 8 or 60a in FIG. 10, and hence its variation with static pressure. The membrane preferably will be flexible enough to allow $\Delta d$, such as flex line 62 in FIG. 8, with each $\Delta P$, which is the change in pressure due to a pulsation in the flowing fluid. This $\Delta P$ facilitates the ratio $\Delta I/I$ in Equation C to occur, and hence the elimination by mathematical cancellation of the $I_0$ variable in Equation B.

Figure 13:
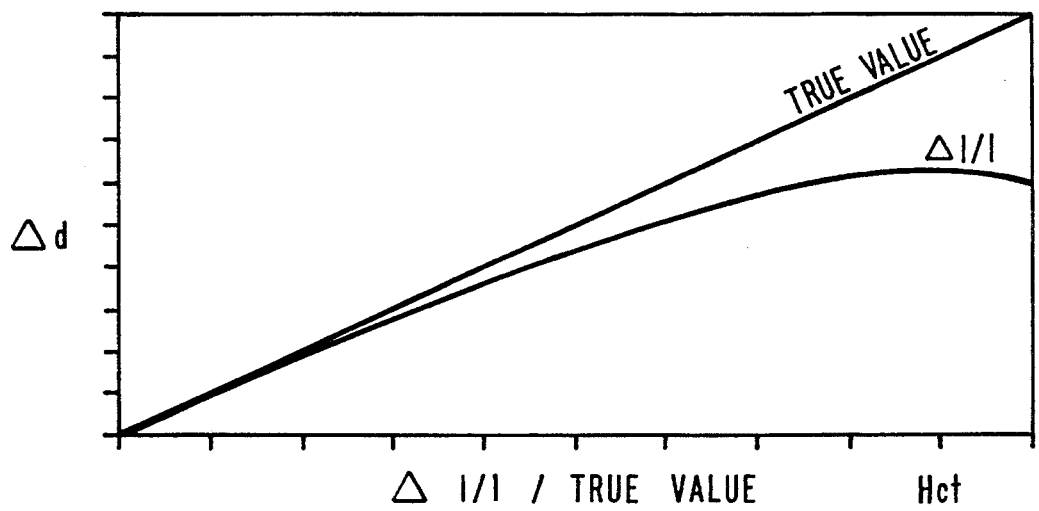
FIG. 13 depicts the error in the $\Delta I/I$ approximation as a function of the changes $\Delta d$ in the blood layer thickness (d) in the cuvette.

Therefore, in order for the inventive extracorporeal disposable cuvette to work in an efficacious manner, it is important that there be a change, $\Delta d$, of d, such as flex line 62 and distance line 60, respectively, in FIG. 8, or such as flex line 62a and distance line 60a, respectively, in FIG. 10. Preferably, $\Delta d$ will be a function of the absolute thickness d of the blood sample, the thickness of the membrane, the area or diameter of the membrane, the change in pressure due to pulses in the fluid and the peak to peak pressure change thereof, or the absolute pressure, and the bulk elastic modulus of the plastic from which the flexible membrane and cuvette are preferably constructed. These parameters allow $\Delta d$ of the flexible membrane in the conduit such that the $\Delta I/I$ in Equation C will be operable, an example of which is depicted in FIG. 12. FIG. 13 shows the error from the true value if $\Delta d$ is improperly selected.

3. Electronic Aspects of the System

The electronic components disclosed in The Incorporated Technique are essentially the same as would be used herein with respect to the integrated circuits, the photoemitters, and the photodetectors. Similar analog and digital schematics and sensor electronics would also be used herein in conjunction with the presently disclosed invention.

4. Blood Volume Determination

In order to use the equations presented herein and in The Incorporated Technique, the determination of intravascular blood volume change during hemodialysis using the hematocrit value requires that the assumption which follow be made. In the case of renal dialysis, as the blood is passing by the dialyzing membrane, it is assumed that no red corpuscles pass through the dialyzing membrane. Only the plasma or watery fluids, electrolytes, and small molecules will pass through the dialyzing membrane. Consequently, any change in the hematocrit value due to dialysis can be shown to be inversely proportional to the blood volume by the EQUATIONS D through F which follow.

$$PCV = \frac{RBC}{BV} \qquad \text{EQUATION D}$$

$$\frac{PCV_1}{PCV_2} = \frac{RBC_1/BV_1}{RBC_2/BV_2} \qquad \text{EQUATION E}$$

$$\frac{Hct_1}{Hct_2} = \frac{BV_2}{BV_1} \qquad \text{EQUATION F}$$

Where:
$PCV_n$ = Packed Cell Volume at time n,
$RBC_n$ = Volume of Red Blood Cells at time n,
$BV_n$ = Volume of Whole Blood at time n, and
$Hct_n$ = Hematocrit value at time n.

Since the red blood cell (RBC) volume is a constant during dialysis, given the assumption that no red cells pass through the dialyzing membrane, then equation F obtains.

By monitoring the change in the hematocrit value at time n to time n+1, the blood volume change over that same period of time is seen. Specifically, as one monitors the rate of change of blood volume of a patient over time while on dialysis, one can also determine the rate of plasma refilling in that given patient. This system enables accurate monitoring of the hematocrit value, in order to accurately determine and monitor the percentage change in blood volume, which relates directly to the rate of plasma refilling as a person undergoes dialysis. Knowing this parameter, the clinician is able to adjust, in real time, the ultrafiltration rate in order to neither under-dialyze nor over-dialyze a patient.

As the foregoing discussion has related to the non-invasive analysis of blood hematocrit information, it will be appreciated that the above mentioned emitter/sensor circuitry are adapted for in vitro analysis of this blood hematocrit value as well.

The principles within the scope of this present invention require: (1) the optimization of fixed, spatial, geometric parameters in cuvette and (2) allow, at the same time, the flexible movement ($\Delta d$) of a membrane, and (3) allow for the $\Delta I/I$ calculation of EQUATION C for the rapid and accurate determination of hematocrit and blood volume change. These principles are found within the preferred design.

The conduit of cuvette 10 in the blood tubing system disclosed herein is an optical path where blood flows through the conduit, having the preferable design seen in FIGS. 1 through 8. The conduit allows light to pass from photoemitter 102 to photodetector 104 through the blood sample passing through cuvette 10. Cuvette 10 is designed with a wall 30, which is a flexible membrane, which moves with pulsations from pressure changes in the blood tubing line due to pump 140 which pumps the blood in a pulsatile fashion through the extracorporeal tubing line.

The elements of importance in the cuvette are the thickness of the blood, such as distance 60 in FIG. 8, and the change in the thickness of the blood, such as is shown by flex line 62 in FIG. 8. This change is due to the pulsations created by pump 140, first and second opposing walls 30 and 32 and the areas thereof, and finally the plastic bulk modulus of first wall 30, all of which combine so as to allow first wall 30 to fluctuate with each fluid pulsation.

Across cuvette 10 is placed an emitter/detector apparatus 100. Light is then shined by photoemitter 102 through the blood sample in the conduit and measured at photodetector 104, as shown in FIG. 8. Spectrophotometric techniques are then performed by computer 150 for subsequent real time display of before and after dialysis constituent concentration values. From such values, should the concentration value sought be that of red blood cells, the instantaneous determination of the blood volume change in real time can be derived. Thus, hematocrit values are noninvasively derived by utilizing electromagnetic radiation as an information carrier. The present invention may be used on an extracorporeal disposable conduit system to determine the critical parameter of the intravascular blood volume.

It will also be appreciated that the present invention will also provide a system and apparatus which can provide immediate and continuous blood volume monitoring information of the subject. It further provides non-invasive, continuous information regarding the blood oxygen saturation status of the patient, independent of the hematocrit value of the patient. Even under conditions of low blood perfusion in the patient, the extracorporeal monitoring disclosed herein provides for increased accuracy and easy usage.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A disposable fluid cuvette, defining a fluid passageway for containing and conducting therethrough a fluid flowing under pressure in a pulsatile fashion, comprising:
   a. an inlet;
   b. an outlet;
   c. a conduit, in fluid communication both between and with said inlet and outlet and being comprised of materials which permit transmission of at least two predetermined wavelengths of electromagnetic radiation therethrough, comprising:
      i. first and second opposed walls, having a predetermined separation therebetween, and constraining the pulsatile flowing fluid therebetween; and
      ii. a transducer means, located in said first wall of said conduit, for varying said predetermined separation responsive to pressure pulsations in the fluid.

2. The cuvette as defined in claim 1, wherein said transducer means is comprised essentially of silicone and said second wall is comprised essentially of medical grade plastic.

3. The cuvette as defined in claim 2, wherein said first and second walls have an opposing facing side that is essentially circular in shape.

4. The cuvette as defined in claim 1, wherein the conduit further comprises means, responsive to pressure pulsations in the fluid, for damping the variations of the predetermined separation.

5. The cuvette as defined in claim 1, wherein said conduit further comprises a third wall, said first wall being disposed between said second and third walls, said third wall and said transducer means having a means, situated therebetween and responsive to pressure pulsations in the fluid, for damping the variations of the predetermined separation.

6. The cuvette as defined in claim 5, wherein said damping means is a hermetically sealed chamber.

7. The cuvette as defined in claim 5, wherein said first and second walls have an opposing facing side that is essentially circular in shape.

8. The cuvette as defined in claim 5, wherein said third wall has a convex side facing a side of said first wall.

9. The cuvette as defined in claim 8, wherein said second and third walls are essentially immobile with respect to said transducer means for each pulse of said pulsatile flowing blood.

10. The cuvette as defined in claim 9, wherein first wall is comprised essentially of silicone.

11. The cuvette as defined in claim 5, wherein said conduit means further comprises first, second and third cylindrical members in contact one with the others;
    a. said first member being essentially comprised of silicone and comprising said first wall;
    b. said second member being essentially comprised of medical grade plastic and comprising said second wall; and
    c. said third member being essentially comprised of medical grade plastic and comprising said third wall.

12. The cuvette as defined in claim 11, wherein an external ring-shaped surface extends from said first and third walls.

13. The cuvette as defined in claim 1 wherein said at least two predetermined wavelengths of electromagnetic radiation comprise a first radiation wavelength of 780 nanometers to about 850 nanometers and a second radiation wavelength of about 1200 nanometers to about 1600 nanometers, and wherein said pulsatile flowing fluid is blood.

14. The cuvette as defined in claim 13 wherein said conduit is comprised of materials which permit transmission of electromagnetic radiation therethrough of a third radiation wavelength being of 900 nanometers to about 1000 nanometers, and of a fourth radiation wavelength being of 600 nanometers to about 700 nanometers.

15. The cuvette as defined in claim 1 wherein said at least two predetermined wavelengths of electromagnetic radiation comprise a first radiation wavelength of 520 nanometers to about 600 nanometers and a second radiation wavelength of about 1200 nanometers to about 1600 nanometers, and wherein said pulsatile flowing fluid is blood.

16. The cuvette as defined in claim 14 wherein said conduit is comprised of materials which permit transmission of electromagnetic radiation therethrough of a third radiation wavelength being of 900 nanometers to about 1000 nanometers, and of a fourth radiation wavelength being of 600 nanometers to about 700 nanometers.

17. The cuvette as defined in claim 1 wherein said transducer means is said first wall, and wherein for each pulse of said pulsatile flowing fluid, said first wall makes a resilient fluctuation and said second wall is essentially immobile.

18. The cuvette as defined in claim 1 wherein said conduit has an essentially cylindrical shape with a vertical wall both outside of and in between said first and second walls, said fluid flowing in a pulsatile fashion in contact with both said vertical wall and said first and second walls.

19. The cuvette as defined in claim 18 wherein the volume of said pulsatile flowing fluid in said conduit passing outside said first and second walls is greater than the volume of said pulsatile flowing fluid passing therebetween.

20. The cuvette as defined in claim 18 wherein said first and second walls are essentially parallel.

21. The cuvette as defined in claim 20 wherein said inlet and said outlet share a common longitudinal axis which is parallel to said first and second walls, and said cylindrical conduit has a longitudinal axis that is normal to the shared common longitudinal axis of said inlet and outlet.

22. The cuvette as defined in claim 1 further comprising:
   a. means, extending from said first wall, for receiving a photoemitter; and
   b. means, extending from said second wall, for receiving a photodetector.

23. The cuvette as defined in claim 1 further comprising external ring-shaped surfaces extending from said first and second walls.

24. The cuvette as defined in claim 1 wherein
   a. said first wall has a first external ring-shaped surface extending therefrom;
   b. said first external ring-shaped surface having a second external ring-shaped surface extending therefrom which is concentric to said first external ring-shaped surface; and
   c. said first and second ring-shaped surfaces each having an inner diameter, said inner diameter of said first ring-shaped surface being less than said inner diameter of said second ring-shaped surface.

25. The cuvette as defined in claim 24 wherein said second wall has an external ring-shaped surface extending therefrom having an inner diameter that is greater than the inner diameter of said first ring-shaped surface.

26. The cuvette as defined in claim 25 wherein said external ring-shaped surface extending from said second wall is concentric with said first ring-shaped surface.

27. The cuvette as defined in claim 1 wherein said conduit cyclically increases and decreases the volume of pulsatile flowing fluid therein with each pulse of said pulsatile flowing fluid.

28. The cuvette as defined in claim 1 wherein each said inlet and said outlet further comprises a means for fixedly attaching thereat a catheter having a lumen therethrough in fluid communication with said conduit.

29. The cuvette as defined in claim 28 wherein said means for fixedly attaching is a luer lock connector.

30. A disposable blood cuvette, defining a fluid passageway for containing and conducting therethrough blood flowing under pressure in a pulsatile fashion, comprising:
   a. an inlet;
   b. an outlet;
   c. a conduit, having an essentially cylindrical shape and being in fluid communication both between and with said inlet and outlet and being comprised of materials which permit transmission of at least two predetermined wavelengths of electromagnetic radiation therethrough, comprising:
      i. opposed first and second walls, having a predetermined separation therebetween, and constraining the pulsatile flowing blood therebetween, and wherein for each pulse of said pulsatile flowing blood said first wall makes a resilient fluctuation so as to vary said predetermined separation and said second wall is essentially immobile; and
      ii. a vertical wall, situated both outside and in between said first and second walls, said blood flowing in a pulsatile fashion in contact with both said vertical wall and said first and second walls.

31. The cuvette as defined in claim 30, wherein the conduit further comprises means for damping the resilient fluctuation of the first wall for each pulse of said pulsatile flowing blood.

32. The cuvette as defined in claim 30, wherein said conduit further comprises a third wall, said first wall being disposed between said second and third walls, said first and third walls having a means, situated therebetween, for damping the resilient fluctuation of the first wall for each pulse of said pulsatile flowing blood.

33. The cuvette as defined in 32, wherein said conduit means further comprises first, second and third cylindrical members in contact one with the others;
   a. said first member being essentially comprised of silicone and comprising said first wall;
   b. said second member being essentially comprised of medical grade plastic and comprising said second and vertical walls;
   c. said third member being essentially comprised of medical grade plastic and comprising said third wall.

34. The cuvette as defined in claim 30, wherein the volume of said pulsatile flowing blood in said conduit passing outside said first and second walls is greater than the volume of said pulsatile flowing blood passing therebetween.

35. The cuvette as defined in claim 30 wherein:
   a. said first wall has a first external ring-shaped surface extending therefrom;

b. said first external ring-shaped surface having a second external ring-shaped surface extending therefrom which is concentric to said first external ring-shaped surface; and c. said first and second ring-shaped surfaces each having an inner diameter, said inner diameter of said first ring-shaped surface being less than said inner diameter of said second ring-shaped surface.

36. The cuvette as defined in claim 35 wherein said second wall has an external ring-shaped surface extending therefrom having an inner diameter that is greater than the inner diameter of said first ring-shaped surface.

37. The cuvette as defined in claim 36 wherein said external ring-shaped surface extending from said second wall is concentric with said first ring-shaped surface.

38. The cuvette as defined in claim 30 further comprising:
a. means, extending from said first wall, for receiving a photoemitter; and
b. means, extending from said second wall, for receiving a photodetector.

39. The cuvette as defined in claim 30 wherein said first and second walls are essentially parallel.

40. The cuvette as defined in claim 39 wherein said inlet and said outlet share a common longitudinal axis which is parallel to said first and second walls, and said cylindrical conduit has a longitudinal axis that is normal to the shared common longitudinal axis of said inlet and outlet.

41. The cuvette as defined in claim 30 further comprising external ring-shaped surfaces extending from said first and second walls.

42. The cuvette as defined in claim 30 wherein said conduit cyclically increases and decreases the volume of pulsatile flowing fluid therein with each pulse of said pulsatile flowing fluid.

43. A disposable fluid cuvette, for defining a fluid passageway for containing and conducting therethrough a fluid flowing in a pulsatile fashion, comprising:
a. a first fluid conduit, having an inlet and an outlet and a lumen therebetween;
b. a second fluid conduit, comprised at least in part of materials essentially permitting transmission of at least two predetermined wavelengths of electromagnetic radiation therethrough, and comprising:
 i. an inlet in fluid communication with the outlet of the first fluid conduit;
 ii. means, in contact with said pulsatile flowing fluid, for making a resilient fluctuation with each pulse of said pulsatile flowing fluid in a direction essentially normal to the general direction of movement of the pulsatile flowing fluid; and
 iii. an outlet;
c. a third fluid conduit, having an inlet and an outlet and a lumen therebetween, said inlet of said third fluid conduit being in fluid communication with the outlet of the second fluid conduit.

44. The cuvette as defined in claim 43 wherein said second fluid conduit further comprises a cylinder having opposing closed first and second ends, said first end being said means for making a resilient fluctuation and said second end being immobile with each pulse of said pulsatile flowing fluid.

45. The cuvette as defined in claim 44 wherein said first and second ends are comprised of materials essentially permitting transmission therethrough of said at least two predetermined wavelengths of electromagnetic radiation.

46. The cuvette as defined in claim 44 wherein:
a. said first fluid conduit and said second fluid conduit have a common longitudinal axis; and
b. said cylinder has a longitudinal axis that is normal to the common longitudinal axis of said first and second fluid conduits.

47. The cuvette as defined in claim 44 wherein:
a. said first end has a first external ring-shaped surface extending therefrom;
b. said first external ring-shaped surface having a second external ring-shaped surface extending therefrom which is concentric to said first external ring-shaped surface; and
c. said first and second external ring-shaped surfaces each having an inner diameter, said inner diameter of said first external ring-shaped surface being less than said inner diameter of said second external ring-shaped surface.

48. The cuvette as defined in claim 47 wherein said second end has an external ring-shaped surface extending therefrom having an inner diameter that is greater than the inner diameter of said first external ring-shaped surface.

49. The cuvette as defined in claim 48 wherein said external ring-shaped surface extending from said second end is concentric with said first external ring-shaped surface.

50. The cuvette as defined in claim 44 wherein said cylinder further comprises a sidewall, situated both outside of and between said first and second ends, and wherein said pulsatile flowing fluid contacts said first and second ends and said sidewall of said cylinder.

51. The cuvette as defined in claim 50 wherein the volume of said pulsatile flowing fluid in said second fluid conduit passing outside said first and second ends is greater than the volume of said pulsatile flowing fluid passing therebetween.

52. The cuvette as defined in claim 43 wherein said second fluid conduit further comprises means, in contact with resilient fluctuation means, for damping the resilient fluctuation of said resilient fluctuation means with each pulse of said pulsatile flowing fluid.

53. The cuvette as defined in claim 43 wherein said second fluid conduit cyclically increases and decreases the volume of pulsatile flowing fluid therein with each pulse of said pulsatile flowing fluid.

* * * * *